US009023583B2

United States Patent
Kishioka et al.

(10) Patent No.: US 9,023,583 B2
(45) Date of Patent: May 5, 2015

(54) MONOLAYER OR MULTILAYER FORMING COMPOSITION

(75) Inventors: Takahiro Kishioka, Toyama (JP); Daisuke Sakuma, Funabashi (JP); Shigeo Kimura, Toyama (JP); Hirokazu Nishimaki, Toyama (JP); Tomoya Ohashi, Toyama (JP); Yuki Usui, Toyama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 7 days.

(21) Appl. No.: 13/879,125

(22) PCT Filed: Oct. 7, 2011

(86) PCT No.: PCT/JP2011/073239
§ 371 (c)(1),
(2), (4) Date: Apr. 12, 2013

(87) PCT Pub. No.: WO2012/050065
PCT Pub. Date: Apr. 19, 2012

(65) Prior Publication Data
US 2013/0216956 A1    Aug. 22, 2013

(30) Foreign Application Priority Data

Oct. 14, 2010   (JP) .................................. 2010-231796

(51) Int. Cl.
| | | |
|---|---|---|
| *G03F 7/075* | (2006.01) | |
| *G03F 7/20* | (2006.01) | |
| *G03F 7/30* | (2006.01) | |
| *C07F 7/18* | (2006.01) | |
| *C09D 183/08* | (2006.01) | |
| *G03F 7/16* | (2006.01) | |
| *C08G 77/28* | (2006.01) | |

(52) U.S. Cl.
CPC ................ *G03F 7/0752* (2013.01); *G03F 7/30* (2013.01); *C07F 7/1836* (2013.01); *C09D 183/08* (2013.01); *C08G 77/28* (2013.01); *G03F 7/20* (2013.01); *G03F 7/0751* (2013.01); *G03F 7/165* (2013.01)

(58) Field of Classification Search
None
See application file for complete search history.

(56) References Cited

U.S. PATENT DOCUMENTS

| | | |
|---|---|---|
| 2006/0121390 A1 | 6/2006 | Gonsalves |
| 2007/0093612 A1* | 4/2007 | Perry et al. ................. 525/333.9 |
| 2007/0203312 A1 | 8/2007 | Lee et al. |
| 2011/0003249 A1 | 1/2011 | Bradford et al. |

FOREIGN PATENT DOCUMENTS

| | | | |
|---|---|---|---|
| JP | 2000-239607 | * | 9/2000 |
| JP | A-2004-123907 | | 4/2004 |
| JP | A-2004-530921 | | 10/2004 |
| JP | A-2006-70026 | | 3/2006 |
| JP | A-2008-50321 | | 3/2008 |
| JP | A-2008-116629 | | 5/2008 |
| JP | A-2008-523053 | | 7/2008 |
| JP | A-2010-209259 | | 9/2010 |
| WO | WO 2009/111122 A2 | | 9/2009 |
| WO | WO 2010/071155 A1 | | 6/2010 |

OTHER PUBLICATIONS

Chemical Abstract (accession No. 2000:619560)—English abstract for JP2000-239607 (2000).*
Machine-assisted English translation for JP2000-239607, provided by JPO (2000).*
International Search Report issued in International Patent Application No. PCT/JP2011/073239 dated Dec. 13, 2011.
Written Opinion issued in International Patent Application No. PCT/JP2011/073239 dated Dec. 13, 2011.

* cited by examiner

*Primary Examiner* — Sin Lee
(74) *Attorney, Agent, or Firm* — Oliff PLC

(57) ABSTRACT

There is provided a composition for forming a monolayer or a multilayer on the substrate. A composition for forming a monolayer or a multilayer containing a silane compound of Formula (1A) or Formula (1B):

$$(R^1O)_3Si\text{-}X\text{-}S(=O)_2\text{-}O\text{-}Z \quad (1A)$$

$$(R^1O)_3Si\text{-}X\text{-}O\text{-}S(=O)_2\text{-}Z \quad (1B)$$

[where $R^1$s are independently a methyl group or an ethyl group; Xs are independently a $C_{1-10}$ linking group; and Zs are independently a $C_{1-10}$ alkyl group or a phenyl group optionally having a substituent, where X optionally contains at least one oxygen atom or sulfur atom in the main chain thereof, and when Z is an alkyl group, at least one hydrogen atom of the alkyl group is optionally substituted with a fluorine atom] and an organic solvent.

7 Claims, 1 Drawing Sheet

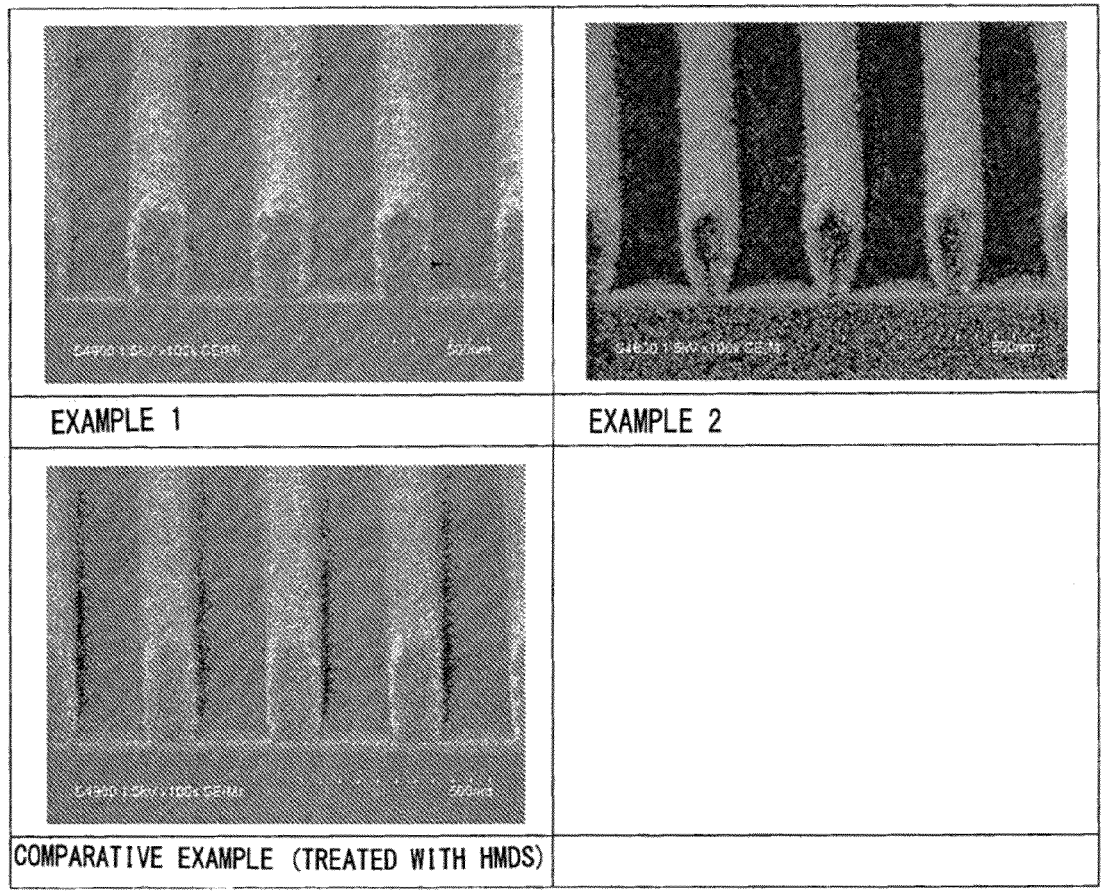

MONOLAYER OR MULTILAYER FORMING COMPOSITION

TECHNICAL FIELD

The present invention relates to a composition applied onto a surface of a substrate to form a monolayer or a multilayer as a resist underlayer. Particularly, the present invention relates to a composition for forming a monolayer or a multilayer on a surface having a level difference (projections and recesses).

BACKGROUND ART

As an ion injecting process in the production of semiconductor devices such as an electric field effect transistor, there may be adopted a process in which an impurity ion for imparting a conductivity type, i.e., an n-type or p-type, is introduced into a semiconductor substrate using a photoresist pattern as a mask. In many cases, the semiconductor substrate has a level difference surface or an uneven surface by forming a gate electrode or a gate wiring on the substrate using a semiconductor material or a metal material such as polycrystal silicon, aluminum, and titanium nitride. When a photoresist pattern is formed on the substrate surface having a level difference (projections and recesses), a photoresist film is formed partially in a large thickness and is difficult to be formed in a homogeneous thickness. Therefore, even after exposure, development, and rinse of the photoresist film, a portion formed in a large thickness is not completely removed and tends to remain. As a result, a bottom shape of a resist pattern often becomes a footing shape and generation of a residue becomes a problem.

Conventionally known is a method for making a surface of a silicon wafer as a representative example of the semiconductor substrate hydrophobic (water repellent) by treating the surface with hexamethyldisilazane (HMDS). The silicon wafer surface exhibits hydrophilicity when a natural oxide film is formed on the surface. The above method for making the surface of the silicon wafer hydrophobic is performed because a photoresist film formed by applying a photoresist solution onto the hydrophilic surface and prebaking the resultant coating has poor adhesion with the silicon wafer.

Hydrophilicity and hydrophobicity of a substrate surface can be evaluated on the basis of a contact angle of the surface with water. Patent Document 1 discloses a photodegradable coupling agent for generating a structure with a contact angle largely changed between before and after light irradiation. The structure is liquid repellent before light irradiation and becomes hydrophilic when irradiated with light due to dissociation of a liquid repellent group. Patent Document 2 discloses a compound for forming an organic thin film capable of selectively changing the surface physical properties by being irradiated with light in order to cause a pattern forming process to be simple and to have high reliability.

PRIOR ART DOCUMENTS

Patent Documents

Patent Document 1: Japanese Patent Application Publication No. 2008-050321 (JP 2008-050321 A)
Patent Document 2: Japanese Patent Application Publication No. 2006-070026 (JP 2006-070026 A)

SUMMARY OF THE INVENTION

Problem to be Solved by the Invention

The present invention provides a novel composition that enables formation of a desired photoresist pattern, of which bottom shape does not become a footing shape even when the photoresist pattern is formed on a substrate surface having a level difference, that is used for a surface treatment of the substrate on which the photoresist pattern is formed, and that is for forming a monolayer or a multilayer on the substrate.

Means for Solving the Problem

The inventors of the present invention have found that by forming a monolayer or a multilayer on a substrate using the composition according to the present invention and forming thereon a photoresist pattern, a bottom shape of the photoresist pattern can be adjusted. That is, a first aspect of the present invention is a composition for forming a monolayer or a multilayer containing a silane compound of Formula (1A) or Formula (1B):

[where $R^1$s are independently a methyl group or an ethyl group; Xs are independently a $C_{1\text{-}10}$ linking group; and Zs are independently a $C_{1\text{-}10}$ alkyl group or a phenyl group optionally having a substituent, where X optionally contains at least one oxygen atom or sulfur atom in the main chain thereof, and when Z is an alkyl group, at least one hydrogen atom of the alkyl group is optionally substituted with a fluorine atom] and an organic solvent.

The monolayer or multilayer forming composition may further contain a silane compound of Formula (2):

[where $R^2$s are independently a methyl group or an ethyl group; and Y is a $C_{1\text{-}5}$ alkyl group optionally having a substituent or a phenyl group optionally having a substituent].

When the $C_{1\text{-}5}$ alkyl group has a substituent, examples of the substituent include an amino group, an imidazolyl group, a pyridyl group, a mercapto group, and a sulfo group. Here, in the amino group "—$NH_2$", at least one hydrogen atom on the nitrogen atom may be substituted with an alkyl group, for example, a methyl group. When the phenyl group has a substituent, examples of the substituent include a methyl group.

A second aspect of the present invention is a method for forming a photoresist pattern including a process of forming a monolayer or a multilayer on a semiconductor substrate using the composition according to the first aspect of the present invention, a process of forming a photoresist film on the monolayer or the multilayer, a process of exposing the semiconductor substrate coated with the monolayer or the multilayer and the photoresist film to light, and a process of developing the photoresist film after the exposure.

As the semiconductor substrate, a substrate, on the surface of which a level difference is formed, can be used. The level difference is caused, for example, by a gate electrode and a gate wiring of the semiconductor device.

Effects of the Invention

The composition according to the present invention can form a monolayer or a multilayer on a surface of a substrate, particularly, a surface of a substrate on which a level difference is formed. The monolayer or the multilayer can adjust a bottom shape of a photoresist pattern formed on the monolayer or the multilayer, for example, so as not to form a photoresist pattern having a footing shape as a bottom shape.

BRIEF DESCRIPTION OF THE DRAWINGS

FIG. 1 is cross-sectional views of photoresist patterns of Example 1, Example 2, and Comparative Example observed under a seaming electron microscope (SEM).

MODES FOR CARRYING OUT THE INVENTION

The composition according to the present invention contains a silane compound of Formula (1A) or Formula (1B). Because the silane compound has a structure of these formulae, the silane compound reacts with an acid to newly generate an acid. For example, when a silane compound of Formula (1B) has a tosyl group, the silane compound reacts with an acid to generate p-toluenesulfonic acid. By the generated acid, the reaction is further accelerated and an acid is productively generated. In Formula (1A) or Formula (1B), examples of the $C_{1-10}$ linking group of X include an alkylene group, a phenylene group, and a cyclohexylene group. When the linking group is a $C_3$ or more alkylene group, the main chain thereof may be branched. In Formula (1A) or Formula (1B), when Z is a phenyl group having a substituent, examples of the substituent include a methyl group. When Z is a $C_3$ or more alkyl group, the alkyl group is preferably a branched alkyl group such as an isopropyl group and a tert-butyl group.

By containing, in addition to the silane compound of Formula (1A) or Formula (1B), a silane compound of Formula (2), the composition according to the present invention can control the hydrophobicity of the surface of the monolayer or the multilayer formed on the substrate. The silane compounds of Formula (2) may be used individually or in combination of two or more types thereof. The ratio of the silane compound of Formula (2) is, for example, 1% by mass to 99% by mass or 5% by mass to 95% by mass, or for example 10% by mass or more and less than 95% by mass, based on the sum total of the mass of the silane compound of Formula (1A) or Formula (1B) and the mass of the silane compound of Formula (2).

The composition according to the present invention may contain, besides the above silane compounds, water and an organic acid. Containing water and an organic acid, the composition according to the present invention can enhance the preservation stability of the composition, and accelerate a condensation reaction of the silane compound when the composition is applied onto a substrate and is baked to form a monolayer or a multilayer. Examples of the organic acid include a carboxylic acid such as acetic acid, maleic acid, oxalic acid, citric acid, malic acid, and succinic acid.

The composition according to the present invention may contain a surfactant. Examples of the surfactant include: nonionic surfactants, for example polyoxyethylene alkyl ethers such as polyoxyethylene lauryl ether, polyoxyethylene stearyl ether, polyoxyethylene cetyl ether, and polyoxyethylene cetyl ether, polyoxyethylene alkylaryl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorinated surfactants, for example EFTOP (registered trade mark) EF301, EF303, and EF352 (manufactured by Mitsubishi Materials Electronic Chemicals Co., Ltd. (former: JEMCO Inc.)), MEGAFAC (registered trade mark) F171, F173, and R30 (manufactured by DIC Corporation), Fluorad FC430 and FC431 (manufactured by Sumitomo 3M Limited), AsahiGuard (registered trade mark) AG710 and Surflon (registered trade mark) S-382, SC101, SC102, SC103, SC104, SC105, and SC106 (manufactured by Asahi Glass Co., Ltd.); and Organosiloxane polymer KP341 (manufactured by Shin-Etsu Chemical Co., Ltd.). The additive amount of the surfactant is usually 0.2% by mass or less, preferably 0.1% by mass or less, based on the mass of all components of the composition according to the present invention. These surfactants may be added individually or in combination of two or more thereof.

The composition according to the present invention can be prepared by dissolving the above components in an appropriate organic solvent to be used in a homogeneous solution state. Examples of the organic solvent include ethylene glycol monomethyl ether, ethylene glycol monoethyl ether, diethylene glycol monomethyl ether, diethylene glycol monoethyl ether, propylene glycol, propylene glycol monomethyl ether, propylene glycol monopropyl ether, propylene glycol monomethyl ether acetate, propylene glycol propyl ether acetate, methylcellosolve acetate, ethylcellosolve acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methylpyrrolidone. These organic solvents may be used individually or in combination of two or more thereof.

The ratio of the solid content remaining after removing the organic solvent (when water and an organic acid are contained, after removing also these components) from the composition according to the present invention is, for example 0.001% by mass to 10% by mass, preferably 0.1% by mass to 5% by mass.

Hereinafter, the use of the composition according to the present invention is described. Onto a semiconductor substrate (for example, a silicon wafer in which a gate electrode is formed and which may be coated with a silicon oxide film, a silicon nitride film, or a silicon oxide nitride film), the composition according to the present invention is applied by an appropriate coating method such as spinner and coater and then, is baked using heating means such as a hot plate. The conditions for baking are appropriately selected from the baking temperatures of 80° C. to 180° C. and the baking times of 0.3 minute to 10 minutes. Instead of the semiconductor substrate, a silicon nitride substrate, a quartz substrate, a glass substrate (including a non-alkali glass, a low-alkali glass, and a crystallized glass), or a glass substrate on which an ITO film is formed, may also be used.

Then, an excessive silane compound remaining on the semiconductor substrate is removed by a solvent and the semiconductor substrate is dried to form a monolayer or a multilayer. The layer formed using the composition according to the present invention is extremely thin and it is difficult to measure the thickness thereof. Furthermore, it is also difficult to specify whether the layer is a monolayer or a multilayer.

On the monolayer or the multilayer formed on the semiconductor substrate through the above processes, a photoresist film is formed. The formation of the photoresist film can be performed by a general method, for example, by application of a photoresist solution and baking thereof.

The photoresist solution is not particularly limited so long as the photoresist solution is sensitive to light for exposure.

Examples of the photoresist include: a positive-type photoresist containing a novolac resin and a 1,2-naphthoquinonediazidesulfonic acid ester; a negative-type photoresist that is a system containing a hydroxy group-containing polymer, an aminoplast crosslinking agent, and a photoacid generator in which a crosslinkage is generated by an acid to lower alkali dissolving rate; a chemical amplification type photoresist containing a binder having a group elevating alkali dissolving rate by being decomposed by an acid, and a photoacid generator; a chemical amplification type photoresist containing a low molecule compound elevating alkali dissolving rate of a photoresist by being decomposed by an acid, an alkali-soluble binder, and a photoacid generator; and a chemical amplification type photoresist containing a binder having a group elevating alkali dissolving rate by being decomposed by an acid, a low molecule compound elevating alkali dissolving rate of a photoresist by being decomposed by an acid, and a photoacid generator. A resist sensitive to an electron beam or extreme ultraviolet (EUV) may also be used.

When the photoresist pattern is formed, exposure is performed through a photomask (reticle) in which a predetermined pattern is formed. For exposure, a KrF excimer laser, an ArF excimer laser, EUV, an electron beam, or the like can be used. After exposure, if necessary, post exposure bake is performed. The conditions for post exposure bake are appropriately selected from heating temperatures of 80° C. to 150° C. and heating times of 0.3 minutes to 60 minutes. To the semiconductor substrate on which the photoresist film is formed, exposure is performed through a photomask and then, development is performed with an alkaline developer.

Examples of the alkaline developer include alkaline aqueous solutions, for example, aqueous solutions of alkali metal hydroxides such as potassium hydroxide and sodium hydroxide, aqueous solutions of quaternary ammonium hydroxides such as tetramethylammonium hydroxide, tetraethylammonium hydroxide, and choline, and aqueous solutions of amines such as ethanolamine, propylamine, and ethylenediamine. Furthermore, to these developers, a surfactant and the like can be added.

The conditions for the development are appropriately selected from development temperatures of 5° C. to 50° C. and development times of 10 seconds to 300 seconds. A resist underlayer film formed from the resist underlayer film forming composition of the present invention can be easily developed at room temperature using a 2.38% by mass tetramethylammonium hydroxide aqueous solution commonly used for the development of the photoresist.

Hereinafter, specific examples of the composition according to the present invention are described but the examples should not be construed as limiting the scope of the present invention.

EXAMPLE

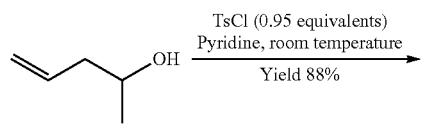

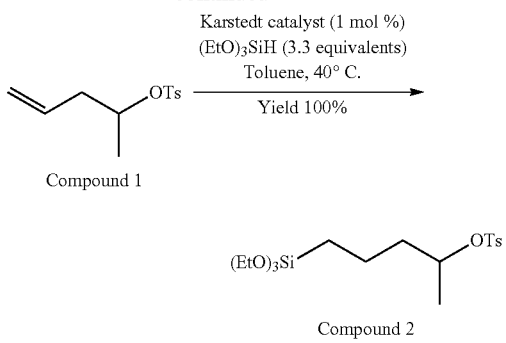

Synthesis Example 1

Into a 300 mL four-neck flask equipped with a magnetic stirrer, 18.00 g of 4-penten-2-ol and 108.00 g of pyridine were charged and the resultant mixture was stirred at room temperature. Next, to the mixture, 37.90 g of p-toluenesulfonyl chloride (TsCl) was added and the resultant mixture was stirred at room temperature for 15 hours. "Ts" is a tosyl group (p-toluenesulfonyl group). After completion of the reaction, the reaction mixture was diluted with 200 g of ethyl acetate and the organic phase was washed with 100 g of pure water three times and with 100 g of saturated saline solution once. Furthermore, 18.00 g of sodium sulfate was added to the organic phase to dry the organic phase. Then, sodium sulfate was filtered to be removed and the filtrate was concentrated and dried to obtain 41.73 g of the above Compound 1 (yield: 88%).

$^1$H-NMR (CDCl$_3$, 400 MHz): 1.26 ppm (d, J=6.4 Hz, 3H), 2.22-2.40 ppm (m, 2H), 2.45 ppm (s, 3H), 4.60-4.67 ppm (m, 1H), 5.01-5.06 ppm (m, 2H), 5.54-5.64 ppm (m, 1H), 7.33 ppm (d, J=8.0 Hz, 2H), 7.81 ppm (d, J=8.0 Hz, 2H)

Synthesis Example 2

Into a 100 mL four-neck flask equipped with a magnetic stirrer, 5.00 g of the Compound 1 obtained in Synthesis Example 1 and 30.00 g of toluene were charged and the resultant mixture was stirred at room temperature. Next, to the mixture, 2,080 μL of Karstedt catalyst (platinum (0)-1,1,3,3-tetramethyldisiloxane complex 0.1 M xylene solution) was added and then, 12.5 mL of triethoxysilane [(EtO)$_3$SiH] was dropped, followed by stirring the resultant mixture at 40° C. for 8 hours. After completion of the reaction, to the reaction mixture, 0.25 g of TOKUSEI SHIRASAGI activated carbon (manufactured by Japan EnviroChemicals, Ltd.) was added and the resultant reaction mixture was stirred at 40° C. for 1 hour. Then, activated carbon was filtered to be removed and the filtrate was concentrated and dried to obtain 8.41 g (yield: 100%) of the above Compound 2 corresponding to the silane compound of Formula (1B).

$^1$H-NMR (CDCl$_3$, 400 MHz): 0.50-0.58 ppm (m, 2H), 1.21 ppm (t, J=6.8 Hz, 9H), 1.25 ppm (d, J=6.4 Hz, 3H), 1.27-1.48 ppm (m, 2H), 1.50-1.70 ppm (m, 2H), 2.44 ppm (s, 3H), 3.79 ppm (q, J=6.8 Hz, 6H), 4.61 ppm (hex, J=7.2 Hz, 1H), 7.32 ppm (d, J=8.0 Hz, 2H), 7.79 ppm (d, J=8.0 Hz, 2H)

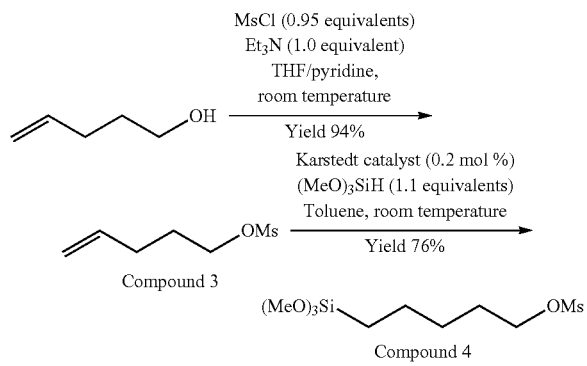

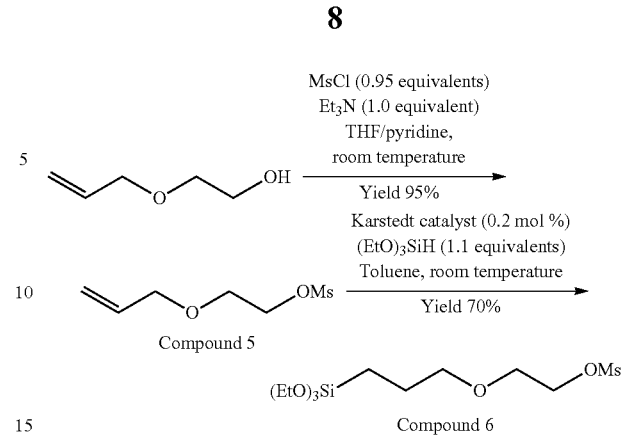

Synthesis Example 3

Into a 200 mL four-neck flask equipped with a magnetic stirrer, 10.00 g of 4-penten-1-ol, 11.75 g of triethylamine (Et$_3$N), 10.00 g of pyridine, and 60.00 g of tetrahydrofuran (hereinafter, in the present specification, abbreviated as THF) were charged and the resultant mixture was stirred at room temperature. Next, to the mixture, 12.63 g of methanesulfonyl chloride (MsCl) was added and the resultant mixture was stirred at room temperature for 18 hours. "Ms" is a mesyl group (methanesulfonyl group). After completion of the reaction, the reaction mixture was diluted with 150 g of ethyl acetate and a deposited salt was filtered to be removed. Next, the filtrate was washed with 70 g of pure water twice and the organic phase was concentrated and dried to obtain a crude product. The crude product was purified with a silica gel column (eluent: ethyl acetate) to obtain 16.99 g (yield: 94%) of the above Compound 3.

$^1$H-NMR (CDCl$_3$, 400 MHz): 1.86 ppm (quintet, J=6.4 Hz, 2H), 2.20 ppm (q, J=6.8 Hz, 2H), 3.01 ppm (s, 3H), 4.24 ppm (t, J=6.4 Hz, 2H), 5.03 ppm (dd, J=10.8 Hz, 2.0 Hz, 1H), 5.07 ppm (dd, J=16.8 Hz, 2.0 Hz, 1H), 5.78 ppm (ddt, J=16.8 Hz, 10.8 Hz, 6.8 Hz, 1H)

Synthesis Example 4

Into a 200 mL four-neck flask equipped with a magnetic stirrer, 10.00 g of the Compound 3 obtained in Synthesis Example 3 and 60.00 g of toluene were charged and the resultant mixture was stirred at room temperature. Next, to the mixture, 1,220 μL of Karstedt catalyst (platinum (0)-1,1,3,3-tetramethyldisiloxane complex 0.1 M xylene solution) was added and then, 8.5 mL of trimethoxysilane [(MeO)$_3$SiH] was dropped, followed by stirring the resultant mixture at room temperature for 18 hours. After completion of the reaction, to the reaction mixture, 0.5 g of TOKUSEI SHIRASAGI activated carbon (manufactured by Japan EnviroChemicals, Ltd.) was added and the resultant reaction mixture was stirred at 40° C. for 30 minutes. Then, activated carbon was filtered to be removed and the filtrate was concentrated and dried to obtain 17.44 g (yield: 76%) of the above Compound 4 corresponding to the silane compound of Formula (1B).

$^1$H-NMR (CDCl$_3$, 400 MHz): 0.65-0.67 ppm (m, 2H), 1.44-1.47 ppm (m, 4H), 1.72-1.78 ppm (m, 2H), 3.00 ppm (s, 3H), 3.57 ppm (s, 9H), 4.22 ppm (t, J=6.4 Hz, 2H)

Synthesis Example 5

Into a 200 mL four-neck flask equipped with a magnetic stirrer, 12.34 g of ethylene glycol monoallyl ether, 12.23 g of triethylamine, 12.34 g of pyridine, and 74.00 g of THF were charged and the resultant mixture was stirred at room temperature. Next, to the mixture, 12.63 g of methanesulfonyl chloride was added and the resultant mixture was stirred at room temperature for 1 hour. After completion of the reaction, the reaction mixture was diluted with 150 g of ethyl acetate and a deposited salt was filtered to be removed. Next, the filtrate was washed with 100 g of pure water twice and the organic phase was concentrated and dried to obtain a crude product. The crude product was purified with a silica gel column (eluent: ethyl acetate) to obtain 19.55 g (yield: 95%) of the above Compound 5.

$^1$H-NMR (CDCl$_3$, 400 MHz): 3.07 ppm (s, 3H), 3.70-3.73 ppm (m, 2H), 4.05 ppm (ddd, J=5.7 Hz, 1.6 Hz, 1.2 Hz, 2H), 4.37-4.40 ppm (m, 2H), 5.21 ppm (ddt, J=10.4 Hz, 1.8 Hz, 1.2 Hz, 1H), 5.28 ppm (ddt, J=17.2 Hz, 1.8 Hz, 1.6 Hz, 1H), 5.89 ppm (ddt, J=17.2 Hz, 10.4 Hz, 5.7 Hz, 1H)

Synthesis Example 6

Into a 100 mL four-neck flask equipped with a magnetic stirrer, 3.00 g of the Compound 5 obtained in Synthesis Example 5 and 18.00 g of toluene were charged and the resultant mixture was stirred at room temperature. Next, to the mixture, 333 μL of Karstedt catalyst (platinum (0)-1,1,3,3-tetramethyldisiloxane complex 0.1 M xylene solution) was added and then, 3.3 mL of triethoxysilane was dropped, followed by stirring the resultant mixture at room temperature for 16 hours. After completion of the reaction, to the reaction mixture, 0.15 g of TOKUSEI SHIRASAGI activated carbon (manufactured by Japan EnviroChemicals, Ltd.) was added and the resultant reaction mixture was stirred at 40° C. for 30 minutes. Then, activated carbon was filtered to be removed and the filtrate was concentrated and dried to obtain a crude product. The crude product was subjected to distillation under reduced pressure to distil the crude product under conditions of external temperature 155 to 172° C./pressure 0.5 to 0.6 torr to obtain 3.99 g (yield: 70%) of the Compound 6 corresponding to the silane compound of Formula (1B).

$^1$H-NMR (CDCl$_3$, 400 MHz): 0.61-0.66 ppm (m, 2H), 1.22 ppm (t, J=5.2 Hz, 9H), 1.65-1.75 ppm (m, 2H), 3.07 ppm (s, 3H), 3.47 ppm (t, J=6.4 Hz, 2H), 3.69 ppm (t, J=4.4 Hz, 2H), 3.81 ppm (q, J=5.2 Hz, 6H), 4.37 ppm (t, J=4.4 Hz, 2H)

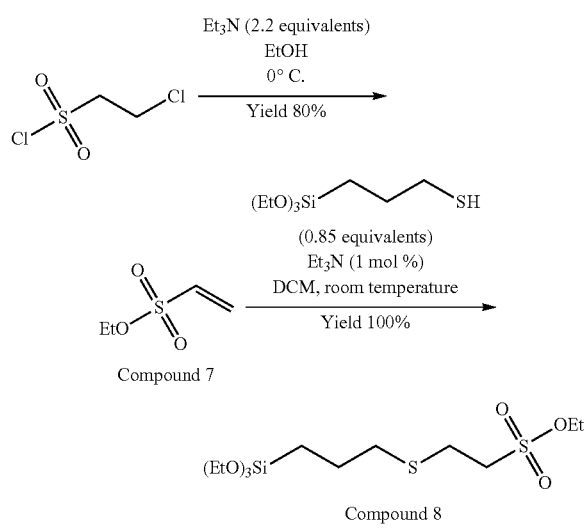

Compound 7

Compound 8

Synthesis Example 7

Into a 500 mL four-neck flask equipped with a magnetic stirrer, 34.13 g of triethylamine and 200 g of ethanol (EtOH) were charged and the resultant mixture was stirred at 0° C. Next, in an ice bath, into the mixture, a solution prepared by diluting 25.28 g of 2-chloroethanesulfonyl chloride with 75 g of 1,2-dichloroethane was dropped and the resultant mixture was stirred at 0 to 10° C. for 4 hours. After completion of the reaction, the reaction mixture was diluted with 500 g of ethyl acetate and the organic phase was washed with 200 g of pure water twice and with 200 g of saturated saline solution once. To the organic phase, two drops of triethylamine and a small amount of BHT (2,6-di-tert-butyl-p-cresol) were added and the organic phase was concentrated and dried to obtain 16.79 g (yield: 80%) of the above Compound 7.

$^1$H-NMR (CDCl$_3$, 400 MHz): 1.40 ppm (t, J=7.0 Hz, 3H), 4.21 ppm (q, J=7.0 Hz, 2H), 6.14 ppm (d, J=9.8 Hz, 1H), 6.40 ppm (d, J=16.6 Hz, 1H), 6.54 ppm (dd, J=9.8 Hz, 16.6 Hz, 1H)

Synthesis Example 8

Into a 200 mL four-neck flask equipped with a magnetic stirrer, 8.00 g of the Compound 7 obtained in Synthesis Example 7, 0.060 g of triethylamine, and 40.00 g of dichloromethane (DCM) were charged and the resultant mixture was stirred at room temperature. Next, in an ice bath, into the mixture, a solution prepared by diluting 11.91 g of mercaptopropyltriethoxysilane with 24.00 g of dichloromethane was dropped and the resultant mixture was stirred at room temperature for 24 hours. After completion of the reaction, the reaction mixture was concentrated and dried to obtain 15.91 g (yield: 100%) of the above Compound 8 corresponding to the silane compound of Formula (1A).

$^1$H-NMR (CDCl$_3$, 400 MHz): 0.71-0.76 ppm (m, 2H), 1.22 ppm (t, J=7.0 Hz, 9H), 1.42 ppm (t, J=7.1 Hz, 3H), 1.68-1.76 ppm (m, 2H), 2.59 ppm (t, J=7.4 Hz, 2H), 2.89-2.94 ppm (m, 2H), 3.30-3.35 ppm (m, 2H), 3.83 ppm (q, J=7.0 Hz, 6H), 4.31 ppm (q, J=7.1 Hz, 2H)

Example 1 to Example 8

Using a silane compound, water, acetic acid, and PGME (propylene glycol monomethyl ether) shown in Table 1 below, a solution was prepared. Then, the solution was filtered using a polyethylene microfilter having a pore diameter of 0.03 μm to prepare a monolayer or multilayer forming composition. In Table 1, "PhTMS" is phenyltrimethoxysilane (manufactured by Tokyo Chemical Industry Co., Ltd.), "pTTMS" is trimethoxy(p-tolyl)silane (manufactured by Gelest, Inc.), and "ImTES" is N-(3-triethoxysilylpropyl)-4,5-dihydroimidazole (manufactured by Gelest, Inc.).

TABLE 1

| | Silane compound | | | Water | Acetic acid | PGME |
| --- | --- | --- | --- | --- | --- | --- |
| | 1 | 2 | 3 | | | |
| Example 1 | Compound 2 0.05 g | PhTMS 0.95 g | | 5 g | 5 g | 89 g |
| Example 2 | Compound 2 0.10 g | PhTMS 0.90 g | | 5 g | 5 g | 89 g |
| Example 3 | Compound 6 0.16 g | pTTMS 0.04 g | | 1 g | 1 g | 17.8 g |
| Example 4 | Compound 6 0.16 g | pTTMS 0.04 g | ImTES 0.001 g | 1 g | 1 g | 17.8 g |
| Example 5 | Compound 6 0.16 g | pTTMS 0.04 g | ImTES 0.03 g | 1 g | 1 g | 17.8 g |
| Example 6 | Compound 8 0.05 g | pTTMS 0.15 g | | 1 g | 1 g | 17.8 g |
| Example 7 | Compound 8 0.05 g | pTTMS 0.15 g | ImTES 0.001 g | 1 g | 1 g | 17.8 g |
| Example 8 | Compound 8 0.05 g | pTTMS 0.15 g | ImTES 0.03 g | 1 g | 1 g | 17.8 g |

[Patterning Test]

Each of the compositions prepared in Examples 1 to 8 was applied onto a silicon wafer using a spin coater and was baked on a hot plate at 100° C. for 1 minute. Then, the baked composition was immersed in OK73 thinner (manufactured by Tokyo Ohka Kogyo Co., Ltd.) composed of 70% by mass of propylene glycol monomethyl ether and 30% by mass of propylene glycol monomethyl ether acetate for 1 minute, was spin-dried, and was dried at 100° C. for 30 seconds to form a monolayer or a multilayer on the silicon wafer. Onto this layer, a commercially available photoresist solution (manufactured by JSR Corporation; trade name: V146G) was applied by a spinner at a revolution number of 950 rpm and was heated on a hot plate at 110° C. for 1 minute to form a photoresist film (film thickness: 0.375 μm). Next, the photoresist film was exposed to light using a KrF scanner (trade name: NSR-S205C; manufactured by Nikon Corporation; wave length: 248 nm, NA: 0.75, ANNULAR) through a mask set so that a line width of the photoresist pattern and the width between the lines both become 0.16 μM after development. Then, the photoresist film was subjected to post exposure bake on a hot plate at 110° C. for 1 minute. The photoresist film was cooled down and was developed using a 0.26 N tetramethylammonium hydroxide aqueous solution as a developer.

After the development, a cross section of each of the obtained photoresist patterns was observed under a scanning electron microscope (SEM). The results using the compositions prepared in Example 1 and Example 2 are shown in FIG.

1. When the composition prepared in Example 1 was used, the shape of the obtained photoresist pattern was observed to have a straight shape. When the composition prepared in Example 2 was used, the shape of the obtained photoresist pattern was observed to have an under-cut shape.

In Comparative Example, the surface of the silicon wafer was treated with hexamethyldisilazane (HMDS) and on the surface, the photoresist pattern was formed by the same method as in Examples. As a result, the shape of the obtained photoresist pattern was a straight shape. That is, by forming the monolayer or the multilayer on the silicon wafer using the composition according to the present invention, the bottom shape of the photoresist pattern formed on the layer could be varied. It is considered that by reacting an acid generated from a photoacid generator contained in the photoresist film with the monolayer or the multilayer having acid propagating effect, an acid such as sulfonic acid is propagated, so that using an action of the acid, the bottom shape of the photoresist pattern could be varied.

The invention claimed is:

1. A composition for forming a monolayer or a multilayer, the composition comprising:
   a silane compound of Formula (1A) of Formula (1B):

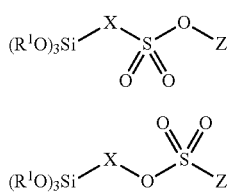

[where $R^1$s are independently a methyl group or an ethyl group; Xs are independently a $C_{1-10}$ linking group; and Zs are independently a $C_{1-10}$ alkyl group or a phenyl group optionally having a substituent, where X contains at least one sulfur atom in the main chain thereof, and when Z is an alkyl group, at least one hydrogen atom of the alkyl group is optionally substituted with a fluorine atom];
   water;
   an organic acid; and
   an organic solvent, wherein the water and the organic acid are provided in the amount sufficient to enhance the preservation stability of the composition and accelerate a condensation reaction of the silane compound when the composition is applied onto a substrate and is baked to form a monolayer or multilayer.

2. The composition for forming a monolayer or a multilayer according to claim 1, further comprising a silane compound of Formula (2):

$(R^2O)_3Si—Y$ (2)

[where $R^2$s are independently a methyl group or an ethyl group; and Y is a $C_{1-5}$ alkyl group optionally having a substituent or a phenyl group optionally having a substituent].

3. A method for forming a photoresist pattern, the method comprising:
   a process of forming a monolayer or a multilayer on a semiconductor substrate using a composition comprising:
   a silane compound of Formula (1A) or Formula (1B):

[where $R^1$s are independently a methyl group or an ethyl group; Xs are independently a $C_{1-10}$ linking group; and Zs are independently a $C_{1-10}$ alkyl group or a phenyl group optionally having a substituent, where X optionally contains at least one oxygen atom or sulfur atom in the main chain thereof, and when Z is an alkyl group, at least one hydrogen atom of the alkyl group is optionally substituted with a fluorine atom]; and
   an organic solvent;
   a process of forming a photoresist film on the monolayer or the multilayer;
   a process of exposing the semiconductor substrate coated with the monolayer or the multilayer and the photoresist film to light; and
   a process of developing the photoresist film after the exposure.

4. The method for forming a photoresist pattern according to claim 3, wherein a level difference is formed on a surface of the semiconductor substrate.

5. The method for forming a photoresist pattern according to claim 3, wherein the composition further comprises water and an organic acid.

6. The method for forming a photoresist pattern according to claim 5, wherein the composition further comprises a silane compound of Formula (2):

$(R^2O)_3Si—Y$ (2)

[where $R^2$s are independently a methyl group or an ethyl group; and Y is a $C_{1-5}$ alkyl group optionally having a substituent or a phenyl group optionally having a substituent].

7. The method for forming a photoresist pattern according to claim 3, wherein the composition further comprises a silane compound of Formula (2):

$(R^2O)_3Si—Y$ (2)

[where $R^2$s are independently a methyl group or an ethyl group; and Y is a $C_{1-5}$ alkyl group optionally having a substituent or a phenyl group optionally having a substituent].

* * * * *